United States Patent [19]
Takemoto et al.

[11] Patent Number: 5,294,714
[45] Date of Patent: Mar. 15, 1994

[54] 2,5-DIOXOPIPERAZINE COMPOUNDS AND METHOD FOR PREPARING α-ASPARTYL-L-PHENYLALANINE METHYL ESTER DERIVATIVES

[75] Inventors: Tadashi Takemoto; Ryoichiro Nakamura, both of Kawasaki, Japan

[73] Assignee: Ajinomoto Co., Inc., Tokyo, Japan

[21] Appl. No.: 965,857

[22] Filed: Oct. 23, 1992

[30] Foreign Application Priority Data

Oct. 23, 1991 [JP] Japan .................. 3-275695

[51] Int. Cl.⁵ .................. C07D 241/04; C07C 229/00
[52] U.S. Cl. .................. 544/385; 560/40; 560/41
[58] Field of Search ............. 544/385; 560/40, 41

[56] References Cited

U.S. PATENT DOCUMENTS

| | | | |
|---|---|---|---|
| 4,579,747 | 4/1986 | Sugiyama | 560/41 |
| 4,673,744 | 6/1987 | Hisamitsu et al. | 544/385 |
| 4,745,210 | 5/1988 | Mita et al. | 560/40 |
| 4,760,164 | 7/1988 | Park et al. | 560/40 |
| 4,778,916 | 10/1988 | Mita et al. | 560/40 |
| 4,780,561 | 10/1988 | Mita et al. | 560/40 |
| 5,144,073 | 9/1992 | Hubbs | 544/385 |

FOREIGN PATENT DOCUMENTS

| | | |
|---|---|---|
| 0196866 | 10/1986 | European Pat. Off. . |
| 0300450 | 1/1989 | European Pat. Off. . |
| 2629201 | 2/1977 | Fed. Rep. of Germany . |
| 2559773 | 8/1985 | France . |
| 1100161 | 4/1989 | Japan .................. 544/385 |
| WO91/14378 | 10/1991 | PCT Int'l Appl. . |

*Primary Examiner*—Cecilia Tsang
*Attorney, Agent, or Firm*—Oblon, Spivak, McClelland, Maier & Neustadt

[57] ABSTRACT

A method of preparing α-APM derivatives without using an expensive L-phenylalanine is provided, wherein 2,5-dioxopiperazine-3-acetamide is reacted with acetic anhydride to give N,N'-diacetyl-6-cyanomethyl-2,5-dioxopiperazine, which is then reacted with benzaldehyde in the presence of a strong base to give 1-acetyl-3-benzylidene-6-cyanomethyl-2,5-dioxopiperazine. This is treated with hydrazine to give 3-benzylidene-6-cyanomethyl-2,5-dioxopiperazine, which is then reduced to prepare 3-benzyl-6-cyanomethyl-2,5-dioxopiperazine, which is converted by reaction with methanol in the presence of a strong acid to an α-APM derivative for use as a sweetener.

18 Claims, No Drawings

2,5-DIOXOPIPERAZINE COMPOUNDS AND METHOD FOR PREPARING α-ASPARTYL-L-PHENYLALANINE METHYL ESTER DERIVATIVES

BACKGROUND OF THE INVENTION

1. Field of the Invention

The present invention relates to a method of preparing 3-benzyl-6-cyanomethyl-2,5-dioxopiperazine, which is an intermediate in the preparation of an α-L-aspartyl-L-phenylalanine methyl ester derivative and to a method of preparing an α-L-aspartyl-L-phenylalanine methyl ester (α-APM) derivative.

2. Discussion of the Background

α-L-aspartyl-L-phenylalanine methyl ester (Aspartame, α-APM) is in heavy demand as a good low-calorie sweetener. The α-APM derivative as referred to herein is a generic name for a group of compounds which include α-APM, α-L-aspartyl-L-phenylalanine dimethyl ester, α-L-aspartyl-L-phenylalanine-β-methyl ester and α-L-aspartyl-L-phenylalanine, each of which can be converted to α-APM with relative ease by conventional methods (see Japanese Patent Application Laid-open Nos. 59-219258 and 59-225152 and U.S. Pat. No. 4,173,562). A variety of methods have previously been proposed for preparing α-APM, which are based on chemically or enzymatically condensing L-aspartic acid or a derivative thereof and L-phenylalanine or a derivative thereof (see *Kirk-Othmer's Encyclopedia of Chemical Technology*, vol. 22, pp 453–458 (1983); R. H. Mazur et al, *J. Med. Chem.*, 91, 2684 (1969); Y. Ariyoshi et al. *Bull Chem. Soc. SpA.* 46, 1893 (1973); Y. Ariyoshi *Kagakuto Seibutsu* 12, 189 (1974); *Chem. Abstr.* 82, 1120u (1975); F. J. Vinick, U.S. Pat. No. 4,256,897; F. J. Vinick et al, *Tetrahedron Lett* 23, 1315 (1982); W.H.J. Boesten, U.S. Pat. No. 3,879,372; G. L. Bachman, U.S. Pat. No. 3,933,781, A. Yasutake et al, *Bull. Chem. Soc. Jpn.* 50, 2413 (1977); Isowa et al., *Tetrahedron Lett.* 20, 7611 (1979)). However, no method of preparing α-APM has been proposed which does not involve the use of L-phenylalanine or a derivative thereof. Such a method would be desirable in order to reduce the production cost of α-APM by eliminating the need to use the expensive L-phenylalanine as raw materials.

SUMMARY OF THE INVENTION

Accordingly, one object of the present invention is to provide a method for preparing α-APM derivatives which does not involve the use of an expensive L-phenylalanine as raw material.

Another object of the present invention is to provide a method of preparing a 3-benzyl-6-cyanomethyl-2,5-dioxopiperazine, which serves as an intermediate which is readily converted into an α-APM derivative.

A further object of the present invention is to provide methods for producing substituted 2,5-dioxopiperazine derivatives which are useful as precursors in the preparation of α-APM derivatives.

Still a further object of the present invention is to provide novel 2,5-dioxopiperazine derivatives useful in the above methods.

These and other objects have been satisfied by the discovery of a method for the synthesis of α-APM derivatives comprising reacting 2,5-dioxopiperazine-3-acetamide, derived from L-aspartic acid, with acetic anhydride, treating the resultant compound with benzaldehyde in the presence of a strong base, followed by hydrazine treatment, and reduction to provide 3-benzyl-6-cyanomethyl-2,5-dioxopiperazine, which is then treated with methanol in the presence of a strong acid to yield the α-APM derivative.

DETAILED DESCRIPTION OF THE PREFERRED EMBODIMENTS

The present invention relates to a method for preparing 3-benzyl-6-cyanomethyl-2,5-dioxopiperazine (I), comprising:

reacting 2,5-dioxopiperazine-3-acetamide (II) with acetic anhydride to provide N,N'-diacetyl-6-cyanomethyl-2,5-dioxopiperazine (III), condensing (III) with benzaldehyde in the presence of a strong base to provide 1-acetyl-3-benzylidene-6-cyanomethyl-2,5-dioxopiperazine (IV), treating (IV) with hydrazine to provide 3-benzylidene-6-cyanomethyl-2,5-dioxopiperazine (V); and reducing (V) to give (I).

An alternative embodiment for this method involves reducing (IV) to provide 1-acetyl-3-benzyl-6-cyanomethyl-2,5-dioxopiperazine (VI), followed by treating (VI) with hydrazine to provide compound (I).

Scheme 1 shows a first embodiment of the present invention in the preparation of (I).

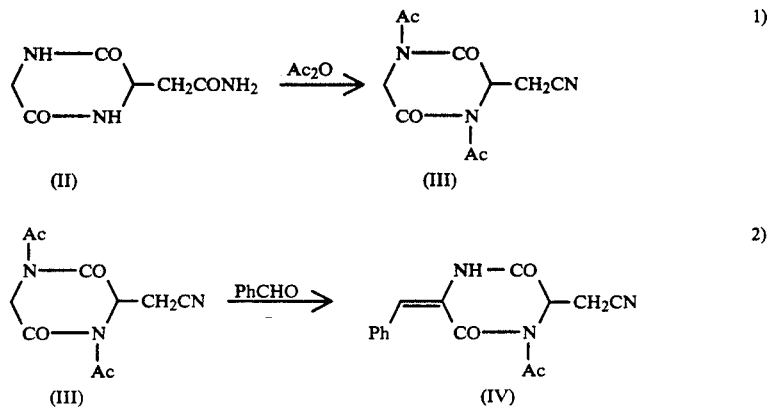

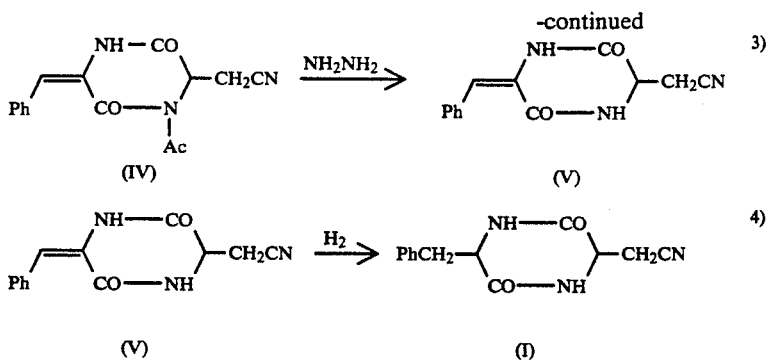

In reaction 1, 2,5-dioxopiperazine-3-acetamide (II) which may be prepared by conventional methods by reaction of L-aspartic acid or its derivative with a protic acid such as monochloroacetic acid, is treated with acetic anhydride to obtain N,N'-diacetyl-6-cyanomethyl-2,5-dioxopiperazine (III). The molar ratio of acetic anhydride to (II) in reaction 1 is 2 or higher, preferably 3 to 10, most preferably 5 to 7. The reaction is performed at a temperature in the range of from 40° C. to 200° C., preferably from 90° C. to 150° C.

In reaction 2, (III) is reacted with benzaldehyde in the presence of a strong base to obtain 1-acetyl-3-benzylidene-6-cyanomethyl-2,5-dioxopiperazine (IV). The molar ratio of benzaldehyde to (III) in reaction 2 is 0.5 or more, preferably from 1.5 to 10. Examples of suitable strong bases include potassium t-butoxide, sodium t-butoxide, lithium diisopropylamide, lithium 2,2,6,6-tetramethylpiperidide, alkali metal amide, alkali metal hydride, and alkali metal triphenyl methyl, preferably potassium t-butoxide. The strong base is used in a molar ratio of strong base to (III) of 0.5 or higher, preferably from 1 to 6, most preferably from 2 to 5.

The solvent used in reaction 2 must be inert to reaction with the raw materials and product. Examples of suitable solvents for reaction 2 include dimethylformamide and t-butanol. The reaction temperature may be from −50° C. to 100° C., preferably from −20° C. to 30° C.

In reaction 3, (IV) is treated with hydrazine to obtain 3-benzylidene-6-cyanomethyl-2,5-dioxopiperazine (V). The amount of the hydrazine to be used in reaction 3 may be an equimolar amount or more relative to (IV) preferably a molar ratio of hydrazine of from 1 to 5, most preferably from 2 to 4. Again the solvent must be inert to reaction with the raw materials and the product. Preferred solvents include dimethyl formamide and lower alkyl ($C_1$–$C_4$) alcohols. Among these, dimethyl formamide and methanol are particularly preferred. Reaction 3 may be performed at any temperature which is sufficient to effect reaction of the hydrazine with (IV), preferably from 0° to 50° C., more preferably from 15° C. to 35° C., most preferably at room temperature (or 18° to 30° C.).

In reaction 4, (V) is catalytically reduced to give (I). The catalyst used in reaction 4 includes conventional catalysts for catalytic reduction. Suitable examples include palladium/carbon, palladium black, platinum/carbon, platinum oxide, nickel, and rhodium-alumina. Palladium/carbon and palladium black are preferred. The solvent must be inert to reaction with the raw materials and the product. Examples of suitable solvents include dimethyl formamide, lower ($C_1$–$C_4$) carboxylic acids, and lower ($C_1$–$C_4$) alkyl alcohols. Among these, dimethylformamide, acetic acid, and methanol are preferred. The reaction temperature is kept low to maintain a sufficient yield and is a temperature in the range of from −78° C. to 100° C., preferably, from −50° C. to 50° C.

In a second embodiment of the present invention, (I) is prepared by the process of scheme 2 below:

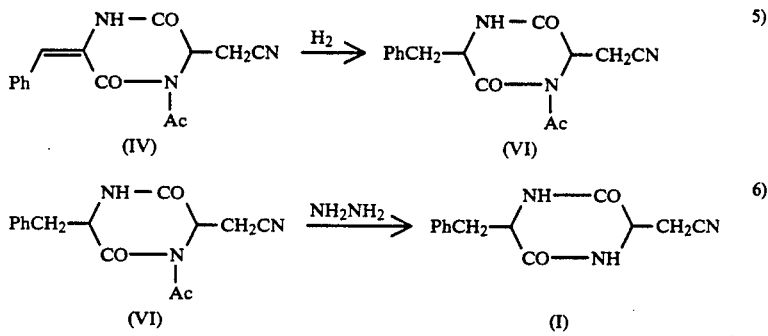

In reaction 5, (IV), as obtained in scheme 1, is catalytically reduced to obtain 1-acetyl-3-benzyl-6-cyanomethyl-2,5-dioxopiperazine (VI). The conditions, solvents, and catalysts for reaction 5 are the same as those used in reaction 4.

In reaction 6, (VI) is treated with hydrazine to obtain (I). The conditions and solvents for reaction 6 are the same as those in reaction 3.

In another embodiment of the present invention, (I) is treated with methanol in the presence of a strong acid to give an α-APM derivative. The solvent methanol to be used may optionally contain a small amount of water, and the molar ratio of the solvent to (I) is desirably 6 or more, preferably 10 to 50, most preferably 15 to 25. If the molar ratio of solvent/(I) is too small, the reaction does not proceed to a sufficient level of completion.

Examples of the strong acid include mineral acids, in liquid or gaseous form, and other acids having pKa's less than 5. Mineral acids such as hydrochloric acid, sulfuric acid or hydrobromic acid are preferred. The equivalent ratio of the acid to (I) is greater than or equal to 0.1 and is preferably within the range of from 0.5 to 15.

Having generally described the present invention, a better understanding can now be gained by reference to the following examples, which are presented for illustrative purposes and are not intended to be limiting unless otherwise specified.

EXAMPLE 1

N,N'-diacetyl-6-cyanomethyl-2,5-dioxopiperazine 360 ml (3.8 mol) of acetic anhydride was added to 10.18 g (0.0595 mol) of 2,5-dioxopiperazine-3-acetamide and stirred at 140° C. for 4.5 hours. The reaction solution was concentrated under reduced pressure, and chloroform and water were added to the residue for liquid-separation and washing. After layer separation, the organic layer was concentrated under reduced pressure, and the residue was dried to obtain 10.54 g of N,N-diacetyl-3-cyanomethyl-2,5-dioxopiperazine. Yield: 74.7%.

$^1$H NMR (CDCl$_3$) $\delta$2.62 (s, 3H), $\delta$2.65 (s, 3H), $\delta$3.12 (d, 2H), $\delta$4.45 (d, 1H), $\delta$5.04 (d, 1H), $\delta$5.29 (t, 1H) MS (FAB):238 (MH+)

EXAMPLE 2

1-Acetyl-3-benzylidene-6-cyanomethyl-2,5-dioxopiperazine:

10.54 g (0.0444 mol) of N,N'-diacetyl-3-cyanomethyl-2,5-dioxopiperazine was dissolved in 200 ml of dimethylformamide, and 18.85 g (0.1776 mol) of benzaldehyde was added. The solution was cooled with ice. A solution of 4.98 g (0.0444 mol) of potassium t-butoxide dissolved in 80 ml t-butanol, was added to the cooled solution.

Afterwards, the reaction system was allowed to warm to room temperature, and stirred for 3.5 hours at room temperature. After cooling the resulting solution with ice, 10 ml of acetic acid was added. Chloroform and water were then added for liquid-separation and washing. The organic layer was concentrated under reduced pressure to obtain a syrup of 1-acetyl-3-benzylidene-6-cyanomethyl-2,5-dioxopiperazine. This was directly used in the next reaction. $^1$H NMR (d$_6$-DMSO) $\delta$2.68 (s, 3H), $\delta$3.07 (dd, 1H), 3.15 (dd, 1H), $\delta$5.18 (t, 1H), 7.28 (s, 1H), 7.45 (m, 5H), 8.19 (bs, 1H) MS (FAB):283 (M+)

EXAMPLE 3

3-Benzylidene-6-cyanomethyl-2,5-dioxopiperazine 100 ml of dimethylformamide was added to the syrup of 1-acetyl-3-benzylidene-6-cyanomethyl-2,5-dioxopiperazine and dissolved, followed by addition of 8.89 g (0.1776 mol) of hydrazine monohydrate. The solution was stirred at room temperature for 3 hours, concentrated, and the residue washed with water to obtain 4.91 g of 3-benzylidene-6-cyanomethyl-2,5-dioxopiperazine. Yield (based on N,N'-diacetyl-3-cyanomethyl-2,5-dioxopiperazine): 45.8%.

$^1$H NMR (d$_6$-DMSO) $\delta$2.90 (dd, 1H), $\delta$3.11 (dd, 1H), $\delta$4.55 (m, 1H) $\delta$6.76 (s, 1H), $\delta$7.40 (m, 5H), $\delta$8.62 (bs, 1H), $\delta$10.29 (bs, 1H) MS (FAB): 242 (MH+).

EXAMPLE 4

3-Benzyl-6-cyanomethyl-2,5-dioxopiperazine 2.91 g (0.0121 mol) of 3-benzylidene-6-cyanomethyl-2,5-dioxopiperazine was dissolved in 80 ml of dimethylformamide and catalytically reduced with hydrogen at room temperature by adding 1.4 g of 10% palladium carbon. After reaction for 4 hours, the catalyst was removed by filtration, and the resulting filtrate was concentrated to obtained 2.68 g of 3-benzyl-6-cyanomethyl-2,5-dioxopiperazine. Yield: 91.5%. $^1$H NMR (d$_6$-DMSO) $\delta$2.13 (dd, 1H), $\delta$2.21 (dd, 1H), $\delta$3.00 (dd, 1H), $\delta$3.14 (dd, 1H), $\delta$4.12 (m, 1H), $\delta$4.29 (m, 1H, $\delta$7.29 (m, 5H), $\delta$8.32 (bs, 1H), $\delta$8.41 (bs, 1H) MS (FAB):244 (MH+) mp:255°–256° C.

EXAMPLE 5

1-Acetyl-3-benzyl-6-cyanomethyl-2,5-dioxopiperazine

The syrup of 1-acetyl-3-benzylidene-6-cyanomethyl-2,5-dioxopiperazine as obtained in Example 2 was dissolved in 100 ml of dimethylformamide, and catalytically reduced with hydrogen at room temperature by adding 2.0 g of 10% palladium carbon. After reaction for 4 hours, the catalyst was removed by filtration, and the resulting filtrate was concentrated under reduced pressure to obtain 5.54 g of 1-acetyl-3-benzyl-6-cyanomethyl-2,5-dioxopiperazine. Yield (based on N,N'-diacetyl-3-cyanomethyl-2,5-dioxopiperazine): 43.5%.

EXAMPLE 6

5.51 g (0.0193 mol) of 1-acetyl-3-benzyl-6-cyanomethyl-2,5-dioxopiperazine was dissolved in 80 ml of dimethylformamide, 3.86 g of hydrazine monohydrate added and the resulting solution stirred for 3 hours at room temperature. The reaction solution was concentrated under reduced pressure, and the residue washed with water to obtain 3.52 g of 3-benzyl-6-cyanomethyl-2,5-dioxopiperazine. Yield: 72.7%.

EXAMPLE 7

2.0 g of 3-benzyl-6-cyanomethyl-2,5-dioxopiperazine was suspended in 40 ml of methanol and heated under reflux for 1.5 hours while 1.8 g of hydrogen chloride was blown into the reaction. 20 ml of concentrated hydrochloric acid was then added and the resulting solution stirred for 4 days at room temperature. The reaction solution was subjected to quantitative analysis by high performance liquid chromatography to determine that the yield of the α-APM derivative was 71.4% (based on 3-benzyl-6-cyanomethyl-2,5-dioxopiperazine).

EXAMPLE 8

2.0 g of 3-benzyl-6-cyanomethyl-2,5-dioxopiperazine was suspended in 50 ml of methanol, 4 ml of 98% sulfuric acid was added, and the resulting solution was heated under reflux for 1.5 hours with stirring. 20 ml of concentrated hydrochloric acid was then added and the solution stirred for an additional 4 days at room temperature. The reaction solution was subjected to quantitative analysis by high performance liquid chromatography to determine that the yield of the α-APM derivative was 70.2% (based on 3-benzyl-6-cyanomethyl-2,5-dioxopiperazine).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for preparing 3-benzyl-6-cyanomethyl-2,5-dioxopiperazine (I), comprising:
    reacting 2,5-dioxopiperazine-3-acetamide (II) with acetic anhydride to provide N,N'-diacetyl-6-cyanomethyl-2,5-dioxopiperazine (III),
    condensing (III) with benzaldehyde in the presence of a strong base to provide 1-acetyl-3-benzylidene-6-cyanomethyl-2,5-dioxopiperazine (IV),
    treating (IV) with hydrazine to provide 3-benzylidene-6-cyanomethyl-2,5-dioxopiperazine (V); and
    reducing (V) to give (I).

2. A method for preparing 3-benzyl-6-cyanomethyl-2,5-dioxopiperazine (I), comprising:
    reacting 2,5-dioxopiperazine-3-acetamide (II) with acetic anhydride to provide N,N'-diacetyl-6-cyanomethyl-2,5-dioxopiperazine (III);
    condensing (III) with benzaldehyde in the presence of a strong base to provide 1-acetyl-3-benzylidene-6-cyanomethyl-2,5-dioxopiperazine (IV);
    reducing (IV) to provide 1-acetyl-3-benzyl-6-cyanomethyl-2,5-dioxopiperazine (VI); and
    treating (VI) with hydrazine to provide (I).

3. A method for preparing an α-L-aspartyl-L-phenylalanine methyl ester compound, comprising:
    treating 3-benzyl-6-cyanomethyl-2,5-dioxopiperazine (I) with methanol in the presence of a strong acid.

4. 3-Benzyl-6-cyanomethyl-2,5-dioxopiperazine.

5. 3-Benzylidene-6-cyanomethyl-2,5-dioxopiperazine.

6. N,N'-Diacetyl-6-cyanomethyl-2,5-dioxopiperazine.

7. 1-Acetyl-3-benzyl-6-cyanomethyl-2,5-dioxopiperazine.

8. 1-Acetyl-3-benzylidene-6-cyanomethyl-2,5-dioxopiperazine.

9. The method of claim 1, wherein said reducing step comprises reduction by addition of hydrogen in the presence of a catalyst selected from the group consisting of palladium/carbon, palladium black, platinum/carbon, platinum oxide, nickel and rhodium-alumina.

10. The method of claim 8, wherein said catalyst is palladium/carbon or palladium black.

11. The method of claim 1, wherein said strong base is selected from the group consisting of potassium t-butoxide, lithium diisopropylamide, lithium 2,2,6,6-tetramethylpiperidide, alkali metal amide, alkali metal hydride, and alkali metal triphenyl methyl.

12. The method of claim 10, wherein said strong base is potassium t-butoxide.

13. The method of claim 3, wherein said strong acid is a mineral acid in liquid or gaseous form or an organic protic acid having a pKa of 5 or less.

14. The method of claim 12, wherein said mineral acid is selected from the group consisting of hydrochloric acid, sulfuric acid and hydrobromic acid.

15. The method of claim 2, wherein said reducing step comprises reduction by addition of hydrogen in the presence of a catalyst selected from the group consisting of palladium/carbon, palladium black, platinum/carbon, platinum oxide, nickel and rhodium-alumina.

16. The method of claim 14, wherein said catalyst is palladium/carbon or palladium black.

17. The method of claim 2, wherein said strong base is selected from the group consisting of potassium t-butoxide, lithium diisopropylamide, lithium 2,2,6,6-tetramethylpiperidide, alkali metal amide, alkali metal hydride, and alkali metal triphenyl methyl.

18. The method of claim 16, wherein said strong base is potassium t-butoxide.

* * * * *